United States Patent [19]
Shimizu et al.

[11] Patent Number: 4,809,699
[45] Date of Patent: Mar. 7, 1989

[54] ELECTROCARDIOGRAPHIC CURRENT DERIVATION ELECTRODE

[75] Inventors: Chuji Shimizu, Funabashi; Yasuaki Onodera, Saitama, both of Japan

[73] Assignee: Fukuda Denshi Co., Ltd., Tokyo, Japan

[21] Appl. No.: 53,784

[22] Filed: May 26, 1987

[30] Foreign Application Priority Data

May 28, 1986 [JP] Japan ............................ 61-080851[U]

[51] Int. Cl.⁴ ............................................. A61B 5/04
[52] U.S. Cl. .................................................. 128/640
[58] Field of Search ............................... 128/639-641, 128/644, 798, 802, 803

[56] References Cited

U.S. PATENT DOCUMENTS

| | | | |
|---|---|---|---|
| 4,522,211 | 6/1985 | Bare et al. | 128/640 |
| 4,674,512 | 6/1987 | Rolf | 128/640 |
| 4,679,563 | 7/1987 | Wada et al. | 128/640 |

*Primary Examiner*—Lee S. Cohen
*Attorney, Agent, or Firm*—Pollock, Vande Sande & Priddy

[57] ABSTRACT

An electrocardiographic current derivation electrode is disclosed, which consists of a substantially rectangular lamination consisting of a resin film, a deposited silver layer formed on one surface of the resin film, a conductive adhesive layer coated on the deposited silver layer and a foamed sheet applied to the outer surface of the resin film. The electrocardiographic current derivation electrode is formed in a substantially central portion thereof with a substantially parallelogrammic terminal. One short side of the terminal is foldably united to the rest of the electrocardiographic current derivation electrode, the other three sides of the terminal are cut sides, and the long cut sides of the parallelogram are not parallel to the long sides of the substantially rectangular electrocardiographic current derivation electrode.

3 Claims, 3 Drawing Sheets

ELECTROCARDIOGRAPHIC CURRENT DERIVATION ELECTRODE

BACKGROUND OF THE INVENTION

1. Field of the Invention

This invention relates to an electrocardiographic current derivation electrode and, more particularly, to an electrocardiographic current derivation electrode for deriving minute current generated in a man in a state secured to the skin of the man.

2. Prior Art

As is well known in the art, electricity is induced in a man by the activities of the heart, brain, muscles, etc.

Particularly, electricity generated in the heart is recorded by an externally provided electrocardiograph as minute voltage induced at the man's skin for effecting diagnosis of the heart. To this end, an input section of the electrocardiograph is electrically coupled to the man. This means that it is necessary to have electrodcardiographic current derivation electrodes in close contact with the man's skin.

A prior art electrocardiographic electrode to be held in close contact with the man's skin will now be described with reference to FIGS. 5 to 7. FIG. 5 is a perspective view of the electrocardiographic electrode 1. The electrode 1 has a substantially circular sticky base 16. The sticky base is a doughnutlike woven cloth having a central opening 17. Its back side has stickiness to be held in close contact with the skin M of a man, as shown in FIG. 7.

An electrode holder 18 made of a hard synthetic resin is bonded to the top side of the sticky base 16 such as to close the opening 17. The electrode holder has a magnetic lead coupler 19 projecting from the top side.

To the underside of the lead coupler 19 is secured an electrode 20, as shown in FIG. 7, for deriving minute current from the heart in direct contact with the skin M of the man.

FIG. 6 shows the back side of a lead connector 21 for leading the minute current in the heart derived from the electrode 20 through the lead 4 to an electrocardiograph (not shown). The lead connector 21 is made of a hard resin and has substantially the same size as the electrocardiographic current derivation electrode 1. The lead connector 21 has a recess 22. An electromagnetic electrode coupler 23 is received in the recess 22 and secured to the lead connector 21. The electrode coupler 23 is connected through a lead 4 to an electrocardiograph (not shown).

For recording an electrocardiogram using the electrocardiographic current derivation electrode 1 having the above construction, cream is preliminarily applied to the skin M of a man to reduce the electric resistance. Then, the sticky base 16 of the electrocardiographic current derivation electrode 1 is bonded to the cream-applied skin M. Subsequently, the magnetic electrode coupler 23 of the lead connector 21 is bonded to the lead coupler 19 of the electrocardiographic current derivation electrode 1, thus coupling the lead connector 21 to the electrocardiographic current derivation electrode 1. In this state, minute voltage derived from the heart by the electrode 20 is supplied through the lead 4 to an electrocardiograph (not shown) for recording.

In the prior art arrangement as described above, magnets are used on both the lead side and the electrode side. Therefore, the arrangement is heavy, and also the structure for supporting the magnets is complicated and large in size, and also it feels hard. For these reasons, the arrangement is unsatisfactory as a tool to be attached to the man's skin, and the cost of manufacture is expensive.

SUMMARY OF THE INVENTION

An object of the invention is to solve the problems that the prior art electrocardiograph current derivation electrode is heavy and complicated in structure, feels heavy and requires high cost of manufacture.

To attain the above object of the invention, there is provided an electrocardiographic current derivation electrode consisting of a substantially rectangular lamination consisting of a resin film, a deposited silver layer formed on one surface of the resin film, a conductive adhesive layer coated on the deposited silver layer and a foamed sheet applied to the outer surface of the resin film, the electrocardiographic current derivation electrode being formed in a substantially central portion thereof with a substantially parallelogrammic terminal, one short side of the terminal being foldably united to the rest of the electrocardiographic current derivation electrode, the other three sides of the terminal being cut sides, the long cut sides of the parallelogram being not parallel to the long sides of the substantially rectangular electrocardiographic current derivation electrode.

When the conductive adhesive coating side surface of the electrocardiographic current derivation electrode according to the invention is applied to the man's skin, the electrocardiographic current derivation electrode is bonded to the skin, and minute electricity generated in the heart or the like of the man flows by encountering low resistance from the skin through the conductive adhesive to the deposited silver layer.

When the substantially parallelogrammic terminal formed in the central portion of the electrocardiographic current derivation electrode is raised by bending it along the short side united to the rest of the electrode, it can be readily clipped.

When the terminal in this state is clipped with a clip or the like, electricity is caused to flow from the deposited silver layer of the terminal as part of the electrocardiographic current derivation electrode to the clip and thence through the lead to an electrocardiograph (not shown).

DETAILED DESCRIPTION OF THE PREFERRED EMBDOIMENTS

Now, the constitution and operation of the electrocardiographic current derivation electrode according to the invention will be described in conjunction with preferred embodiments thereof with reference to the drawings.

Figure 1:
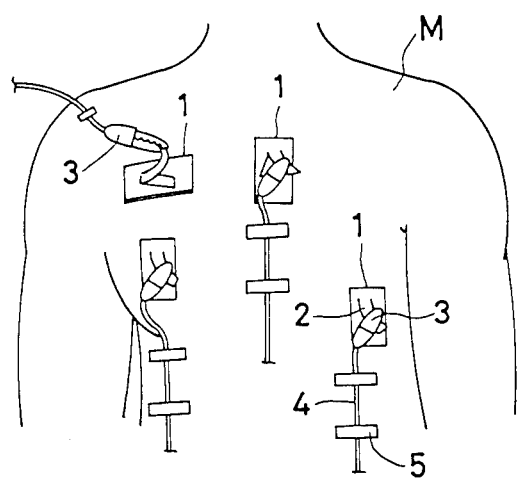
FIG. 1 is a view for explaining an outline of the invention.

FIG. 1 is a view for explaining an outline of the invention. Electrocardiographic current derivation electrodes 1 according to the invention are applied to the skin M of the man. A terminal 2 of each of the electrocardiographic current derivation electrodes 1 is clipped with a clip 3, which is connected through a lead 4 to an external electrocardiograph (not shown).

Reference numeral 5 designates a adhesive tape for securing the lead 4.

Figure 2:
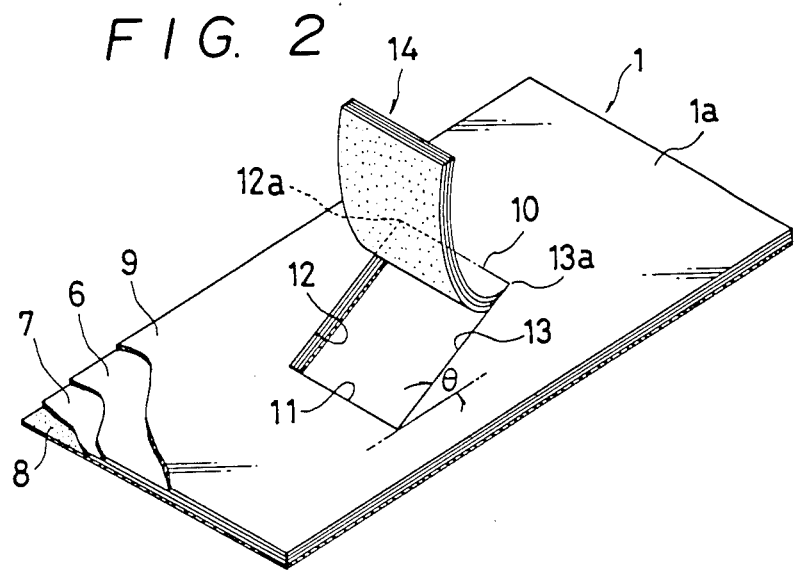
FIG. 2 is a perspective view showing an embodiment of the electrocardiographic current derivation electrode according to the invention.

FIG. 2 is a perspective view showing an embodiment of the electrocardiographic current derivation electrode 1 according to the invention. The electrode 1 is shown partly broken away for the sake of description.

Reference numeral 1a in the FIG. designates a body of the electrocardiographic current derivation electrode 1. The body 1a consists of a polyester resin film 6, a deposited silver layer 7 formed on one surface of the resin film 6 and a conductive adhesive layer 8 coated on the surface of the deposited silver layer 7.

The conductive adhesive 8 as the surface layer permits the electrocardiographic current derivation electrode 1 to be bonded with low resistance to the skin M of the body.

To the other surface of the resin film 6 is bonded by means of an adhesive an independent foamed sheet 9 consisting of butadiene, thus forming the body 1a.

The body 1a is rectangular in shape having short and long sides. The body 1a is provided substantially in a central portion with a substantially parallelogrammic terminal 14 having a foldable short side 10 united to the rest of it, a cut short side 11 as the other short side and cut long sides 12 and 13.

The long sides 12 and 13 of the terminal 14 are not parallel to, i.e., have an angle $\theta$ with respect to, the long sides of the body 1a.

This is done so in order to make the terminal 14 as long as possible so that it can be readily clipped with a clip while also providing a different direction, in which the terminal 14 is pulled, from the cutting direction to reduce the pulling force so as to prevent damage to the stems 12a and 13a of the long sides 12 and 13.

Figure 3:
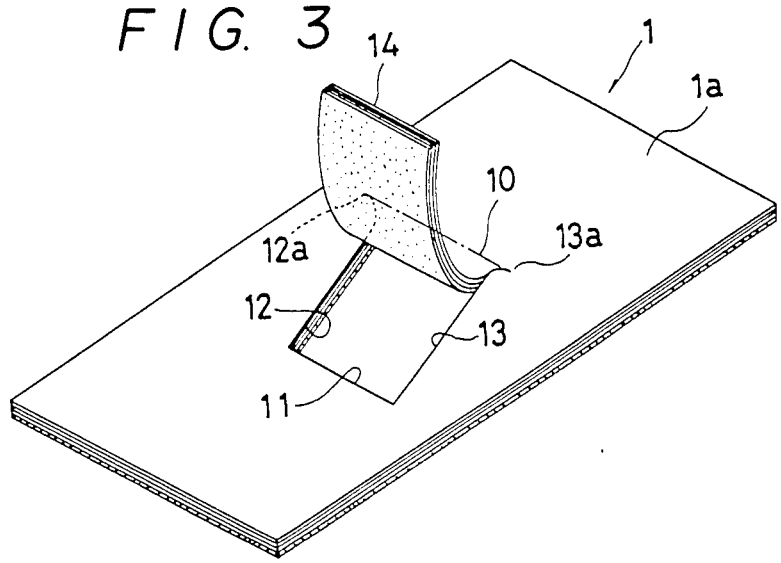
FIG. 3 is a perspective view showing a different embodiment of the electrocardiographic current derivation electrode according to the invention.

FIG. 3 is a perspective view showing a different embodiment of the electrocardiographic current derivation electrode according to the invention. This embodiment is different from the preceding embodiment shown in FIG. 2 in that the long sides 12 and 13 of the terminal 14 have outwardly curved stem portions 12a and 13a terminating in the opposite ends of the short side 10 as the stem of the terminal 14. The width of the terminal 14 thus is increased in the neighborhood of the short side 10. This has an effect of reinforcing the terminal 14.

Figure 4:
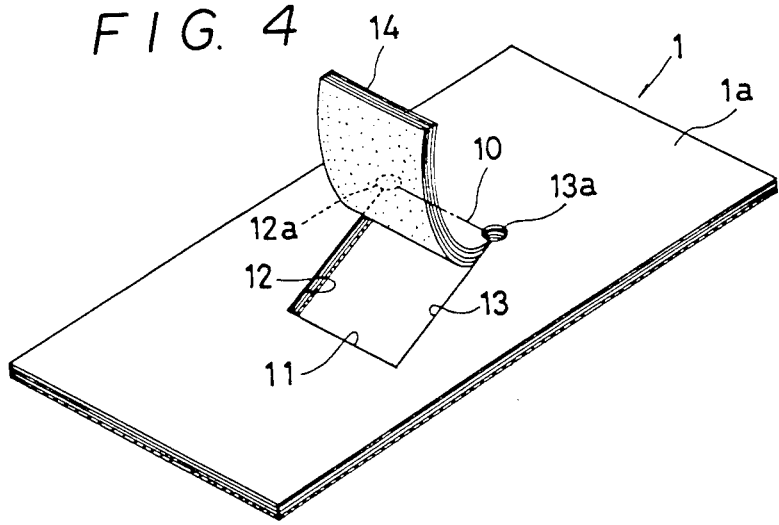
FIG. 4 is a perspective view of showing a further embodiment of the electrocardiographic current derivation electrode according to the invention.
Figure 5:
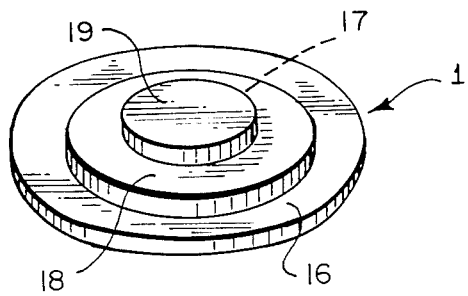
FIG. 5 is a perspective view showing a prior art electrocardiographic current derivation electrode.
Figure 6:
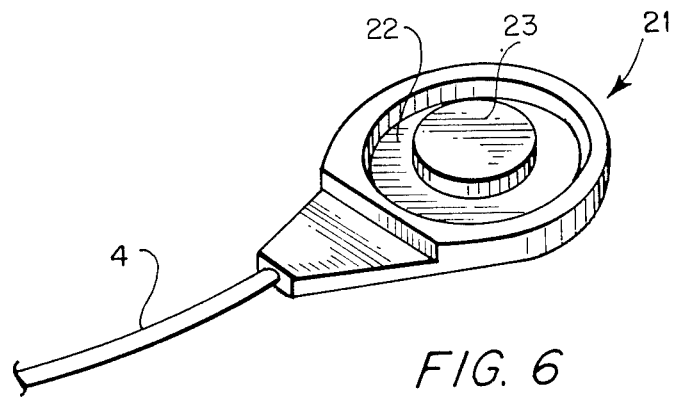
FIG. 6 is a perspective view showing the back side of a prior art lead connector.
Figure 7:
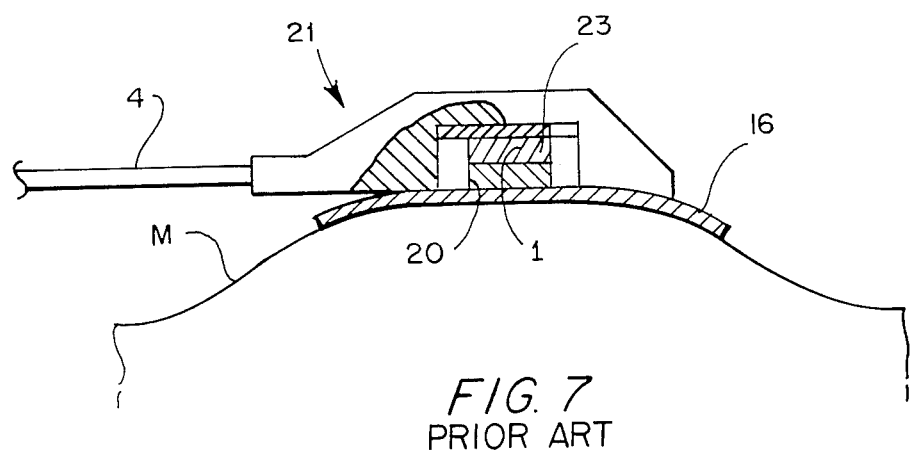
FIG. 7 is a view showing a prior art electrocardiographic current derivation electrode in use.

FIG. 4 is a perspective view showing a further embodiment of the electrocardiographic current derivation electrode according to the invention. This embodiment is different from the embodiment of FIGS. 2 and 3 in that the stem ends 12a and 13a of the long sides 12 and 13, i.e., the opposite ends of the short side 10 as the stem of the terminal 14, are in the form of circular holes.

This arrangement eliminates the wedge effect of the stem ends 12a and 13a and thus has an effect of protecting the terminal 14.

As has been described in the foregoing, according to the invention the terminal body is a lamination consisting of a resin film, a deposited silver layer formed on one surface of the resin film, a conductive adhesive layer coated on the deposited silver layer and a foamed sheet applied to the other surface of the resin film and has a terminal formed by cutting a central portion. Thus, it is simple in construction and is suited for mass production to permit great cost reduction.

Thus, it is possible to use the electrode as a consumable item, and one can use new electrodes at all times. Cleanliness thus can be maintained, and it is possible to prevent infection of diseases from one patient to another.

Further, since the electrode according to the invention uses a conductive adhesive, there is no need of preliminarily applying cream to the skin, so that high operability can be guaranteed.

Further, the entire structure of the electrode according to the invention has a flexible structure so that it can be readily and satisfactorily attached to the skin of the man.

Further, the terminal according to the invention has a double-layer structure consisting of the resin film and foamed sheet which reinforce each other, so that it has high tenacity.

Further, according to the invention the terminal is provided substantially in the central portion of the body, so that it is less liable to be broken apart, and the terminal can be stably used.

Further, the cut long sides of the terminal are inclined with respect to the long sides of the body. This has an effect of increasing its length in the raised state, and it can be readily clipped with a clip. Further, since the direction in which the pulling force is applied is different from the direction of the cut long sides, the pulling force can be reduced to prevent damage to the terminal.

What is claimed is:

1. An electrocardiographic current derivation electrode consisting of a substantially rectangular lamination having a pair of opposing short sides and a pair of opposing long sides, said lamination consisting of a resin film, a deposited silver layer formed on one surface of said resin film, a conductive adhesive layer coated on said deposited silver layer and a foamed sheet applied to the other surface of said resin film, said electrocardiographic current derivation electrode being formed in a substantially central portion thereof with a substantially parallelogrammic terminal, said terminal having first and second opposing short sides and a pair of opposing long sides, said first short side of said terminal being foldably united to the rest of said electrocardiographic current derivation electrode, the other three sides of said terminal being cut sides, the long cut sides of said parallelogrammic terminal being inclined to the long sides of said substantially rectangular lamination and having stem ends at their junction with said first short end.

2. The electrocardiographic current derivation electrode according to claim 1, wherein the long sides of said substantially parallelogrammic terminal have outwardly curved stem ends.

3. The electrocardiographic current derivation electrode according to claim 1, wherein the long sides of said substantially parallelogrammic terminal have stem ends in the form of circular holes.

* * * * *